United States Patent
Doviack et al.

(10) Patent No.: US 10,182,895 B2
(45) Date of Patent: Jan. 22, 2019

(54) PROCESS FOR THE FABRICATION OF DENTAL RESTORATIONS

(71) Applicant: Continental Dental Ceramics, Inc., Torrance, CA (US)

(72) Inventors: Jerry W. Doviack, Pacific Palisades, CA (US); Mikolaj Szafran, Piaseczno (PL); Paulina Wiecinska, Warsaw (PL); Tadeusz Mizerski, Warsaw (PL); Ewa Bobryk, Warsaw (PL); Gabriel Rokicki, Warsaw (PL); Agnieszka Zurawska, Warsaw (PL); Pawel Falkowski, Warsaw (PL); Agnieszka Antosik, Warsaw (PL)

(73) Assignee: CONTINENTAL DENTAL CERAMICS, INC., Torrance, CA (US)

( * ) Notice: Subject to any disclaimer, the term of this patent is extended or adjusted under 35 U.S.C. 154(b) by 16 days.

(21) Appl. No.: 15/597,704

(22) Filed: May 17, 2017

(65) Prior Publication Data
US 2018/0206953 A1    Jul. 26, 2018

Related U.S. Application Data

(60) Provisional application No. 62/497,308, filed on Aug. 22, 2016.

(51) Int. Cl.
*A61C 13/20* (2006.01)
*C04B 35/624* (2006.01)
(Continued)

(52) U.S. Cl.
CPC .......... *A61C 13/20* (2013.01); *A61C 5/77* (2017.02); *A61C 13/0006* (2013.01);
(Continued)

(58) Field of Classification Search
CPC .......... C04B 35/624; C04B 2235/6023; A61C 13/20
See application file for complete search history.

(56) References Cited

U.S. PATENT DOCUMENTS

| | | | | |
|---|---|---|---|---|
| 5,076,980 A | * | 12/1991 | Nogues | ............ C03B 19/12 264/621 |
| 6,383,443 B1 | * | 5/2002 | Jeng | ............ C04B 35/111 264/621 |

(Continued)

FOREIGN PATENT DOCUMENTS

| | | |
|---|---|---|
| PL | 212145 | 9/2008 |
| PL | 213043 | 9/2008 |

OTHER PUBLICATIONS

Ghosal et al. "A Physical Model for the Drying of Gelcast Ceramics". Journal of the American Ceramic Society, vol. 82, Issue 3 (1999) pp. 513-520. (Year: 1999).*

(Continued)

*Primary Examiner* — Erin Snelting
(74) *Attorney, Agent, or Firm* — Karish & Bjorgum, PC

(57) ABSTRACT

Dental restorations are created by preparing a hydrocolloid mold for such dental appliances as crowns and bridges. A slurry of zirconia powder and 3-O-acryloyl-D-glucose is prepared. The slurry is gelcast in the hydrocolloid mold with polymerization of the 3-O-acryloyl-D-glucose to a green body. The green body is dried and machined to the form of the dental restoration. The polymerized 3-O-acryloyl-D-glucose is then burned from the machined green body. The remaining zirconia body in the form of the dental restoration is then sintered to form the finished device.

20 Claims, 1 Drawing Sheet

(51) Int. Cl.
- C04B 35/48 (2006.01)
- C04B 35/64 (2006.01)
- A61C 5/77 (2017.01)
- A61C 13/00 (2006.01)
- C04B 35/636 (2006.01)
- C04B 35/638 (2006.01)

(52) U.S. Cl.
CPC .......... *A61C 13/0022* (2013.01); *C04B 35/48* (2013.01); *C04B 35/624* (2013.01); *C04B 35/636* (2013.01); *C04B 35/638* (2013.01); *C04B 35/64* (2013.01); *C04B 2235/3244* (2013.01); *C04B 2235/6023* (2013.01); *C04B 2235/612* (2013.01); *C04B 2235/6567* (2013.01)

(56) References Cited

U.S. PATENT DOCUMENTS

| | | | |
|---|---|---|---|
| 8,231,825 B2 | 7/2012 | Eriksson et al. | |
| 10,028,809 B2* | 7/2018 | Jahns | A61C 13/0006 |
| 2009/0321971 A1* | 12/2009 | Brodkin | A61C 13/0006 |
| | | | 264/17 |
| 2011/0198218 A1* | 8/2011 | Fuji | C25B 11/035 |
| | | | 204/284 |
| 2015/0238291 A1* | 8/2015 | Hauptmann | A61C 13/0022 |
| | | | 428/64.1 |
| 2016/0312628 A1* | 10/2016 | Kirby | C23C 16/56 |
| 2018/0170812 A1* | 6/2018 | Xu | C04B 35/486 |
| 2018/0186698 A1* | 7/2018 | Yang | C04B 35/10 |

OTHER PUBLICATIONS

Gilissen et al. "Gelcasting, a near net shape technique". Materials and Design, vol. 21, Issue 4 (2000) pp. 251-257. (Year: 2000).*

Wiecinska et al. "L-Ascorbic acid as a new activator in fabrication of ceramics by techniques using in situ polymerization". Journal of the European Ceramic Society, vol. 34, Issue 6 (2014, available online 2013) pp. 1581-1589. (Year: 2013).*

Wiecinska et al. "Organic additives in gel-tape casting of ceramic powders—A novel approach to the problem of elasticity and cracking of thin tapes". Journal of the European Ceramic Society, vol. 35, Issue 14 (2015) pp. 3949-3957. (Year: 2015).*

Bednarek, Paulina et al., Gelcasting of alumnia with a new monomer synthesized from glucose, ScienceDirect Journal of European Ceramic Society 30 (2010) pp. 1795-1801.

* cited by examiner

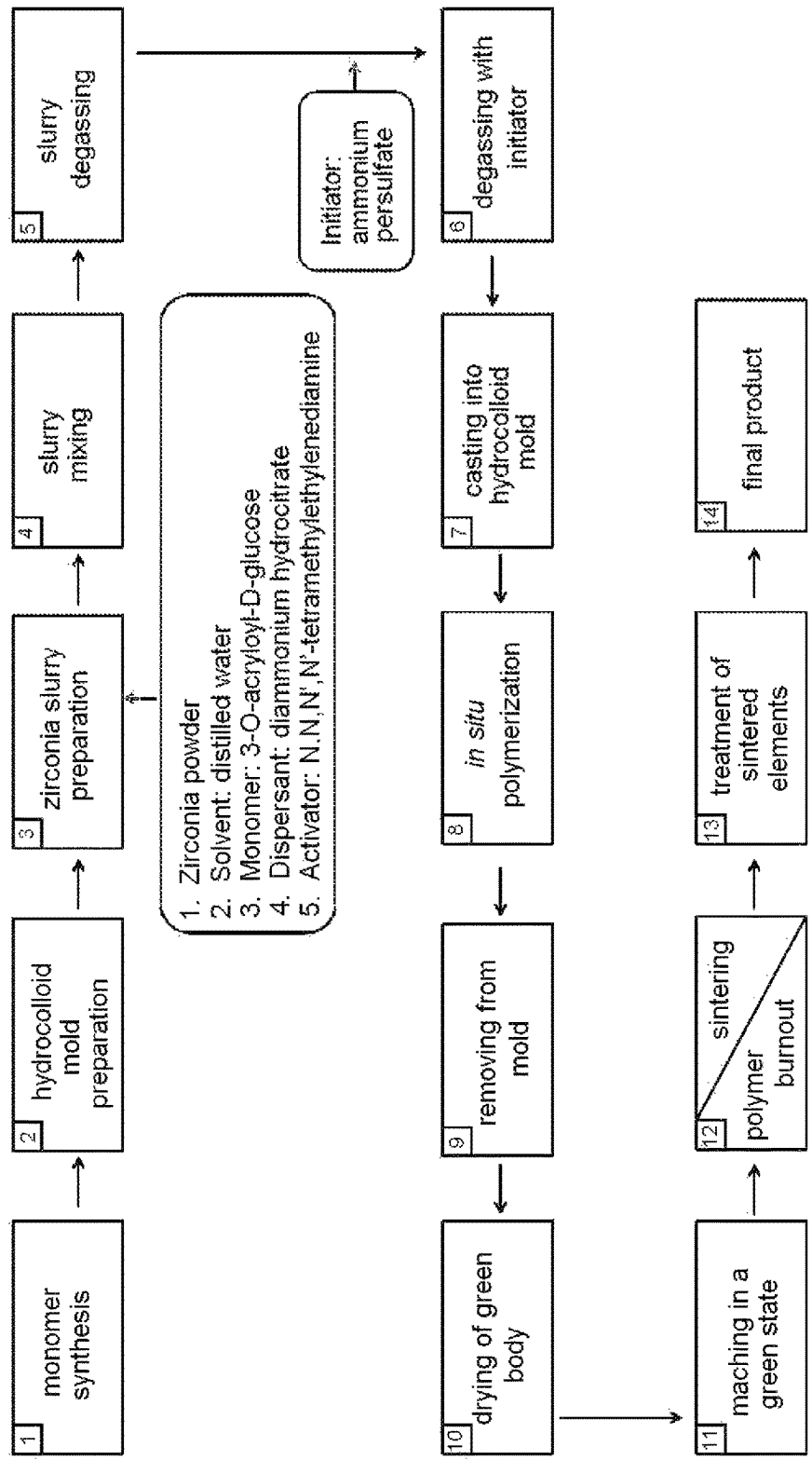

PROCESS FOR THE FABRICATION OF DENTAL RESTORATIONS

BACKGROUND OF THE INVENTION

The field of the present invention is dental restorations.

Dentistry has long involved the creation of replacement appliances such as crowns and bridges for diseased and damaged teeth. Such restorations need to be hard and durable to function as a crown or bridge when mounted in the patient. Properly formed appliances of metal, acrylic resin and ceramics can meet such performance requirements. Among the ceramics, zirconium dioxide (zirconia) is a favored material because of its hard and durable properties. Although favored for dental restorations because of its hardness and durability, fabricating restorations from zirconia can be a time-consuming process with significant material waste, which can exceed 75%.

Dental restorations often begin with an impression of the patient's teeth covering the area of interest. Impressions can be made from a number of materials such as wax, agar based hydrocolloids and the like. From an impression, a casting is created, typically of gypsum, duplicating the area of interest where the impression was taken. In a modern dental lab, a digital scan of the casting is then made and the restoration designed therefrom using computer aided design. A pre-sintered block of zirconia can then be milled using the digital design to create a restoration. The pre-sintered zirconia restoration is then fully sintered. Final touch-up, glazing and coloration may be undertaken as needed before installation in the patient.

SUMMARY OF THE INVENTION

The present invention contemplates the fabrication of sintered zirconia ceramic dental restorations through gelcasting of zirconia suspension containing a monosaccharide based monomer to a green state through polymerization of the monomer. By using a monosaccharide based monomer, toxicity is understood to be reduced or avoided. In the green state prior to sintering, the body can be easily machined if needed to the form of the desired restoration. One such monosaccharide based monomer contemplated with the present invention is 3-O-acryloyl-D-glucose. The gelcasting can also be conveniently accomplished in a hydrocolloid mold. Once properly formed, the body can be sintered into a hard and durable dental restoration.

Proper viscosity and uniform dispersion of ceramic powder in suspension and uniform drying of cast parts before sintering in the gelcasting process are needed for dental quality appliances. The present invention further contemplates protocols insuring that custom dental restorations can be of uniform high quality without the need for machining pre-sintered zirconia blocks.

Accordingly, it is an object of the present invention to provide an improved process for the fabrication of dental restorations such as crowns and bridges. Other and further objects and advantages will appear hereinafter.

BRIEF DESCRIPTION OF THE FIGURE

The FIGURE is a process flow chart for the gel casting of zirconia dental restorations.

DETAILED DESCRIPTION OF THE PREFERRED EMBODIMENT

The process flowchart of the FIGURE presents stages of the fabrication of zirconia dental restorations using gelcasting. The process includes the synthesis of a monomer, Step 1, the preparation of a mold, Step 2, the gelcasting and conditioning of a green body, Steps 3-10, the machining of the green body, Step 11, the polymer burnout and sintering of the green body, Step 12, and the treatment of the post sintered body, Step 13, to a zirconia dental restoration, Step 14. The synthesis of the monomer, Step 1, and the preparation of the mold, Step 2, may be separately undertaken and the products reserved for use. The machining through sintering of the green body to a zirconia crown or bridge, Steps 11-13, may also each be separately undertaken. The gelcasting, from the preparation of the slurry, Step 3, to the drying of the green body, Step 10, is appropriately undertaken as a continuous process.

In the process to create zirconia dental restorations, a monosaccharide based monomer, is used. The monomer of the preferred embodiment is 3-O-acryloyl-D-glucose. This monomer is disclosed in Polish Patent No. 212,145 issued Aug. 31, 2012 to Politechnika Warszawska (Warsaw University of Technology) and Polish Pat. No. 213,043 issued Jan. 31, 2013 to Politechnika Warszawska. The disclosures of these patents are incorporated herein by reference in their entirety.

The synthesis of this organic monomer, Step 1, incorporates the replacement of one of the hydroxyl groups in D-glucose by an acryloyloxy group. This group has a double bond between carbons which enables polymerization of the molecules. The reagents used include:

1,2;5,6-di-O-isopropylidene-D-glucofuranose—DIPG ($C_{12}H_{20}O_6$, 260.29 g/mol);
Acryloyl chloride ($C_3H_3ClO$, 90.51 g/mol);
N,N-dimethylaniline—DMA ($C_8H_{11}N$, 121.18 g/mol);
Methylene chloride (pure) ($CH_2Cl_2$, 84.93 g/mol);
Sulfuric acid (pure 96-98%) ($H_2SO_4$, 98.08 g/mol);
Phenothiazine (pure>98%) ($C_{12}H_9NS$, 199.27 g/mol);
Hexane fraction pure ($C_6H_{14}$, 86.18 g/mol);
Lead carbonate (pure>98%) ($PbCO_3$, 267.21 g/mol);
Magnesium sulfate (pure) ($MgSO_4$, 120.36 g/mol).

Synthesis Occurs in Two Stages.

In the first stage, 3-O-acryloyl-1,2:5,6-di-O-isopropylidene-D-glucofuranose (Acr-DIPG) is synthesized. Looking at the process in order, DIPG, DMA and methylene chloride are placed in the 2000 ml three-necked flask equipped with a condenser (with a drying tube containing $CaCl_2$) and a dropping funnel. The DIPG dissolves entirely, but the reaction mixture clears after heating. Acryloyl chloride is added from the dropping funnel over a period of 70 minutes (temp. of bath 60° C., temp. of reaction mixture 47° C.). Then the mixture is boiled for 48 hours. The contents of the flask are poured into water (3 L) placed in a separator funnel (vol. 5 L). The lower layer is separated and washed two times by 3 L of 5% solution of sulfuric acid, and two times by 3 L of water. The organic solution is dried by magnesium sulfate and concentrated (11 mg of phenothiazine is added to the dried filtrate before the evaporation and 718 ml of methylene chloride is recovered). Then 300 ml of hexane is added and the solution was cooled in a refrigerator. After 24 hours the precipitate is filtered off and dried in the air. The white product obtained is sufficiently pure for the next stage of the synthesis.

In the second stage, the monomer 3-O-acryloyl-D-glucose to be polymerized in the gelcasting is synthesized. Again looking at the process in order, the substrates (Acr-DIPG, sulfuric acid and water) and 6.5 mg of phenothiazine are placed in the reactor and heated to 110° C. After 130 minutes, the reaction mixture is clear and yellowish. After seven hours the reaction is complete. The mixture is cooled and 30 g of lead carbonate is added in one portion in order to neutralize the acidic solution. The mixture is stirred for five minutes then filtered and concentrated in air up to concentration ca. 65%. Then the oleic solution is stored in the refrigerator for 72 hours. The white precipitate is filtered off and dried in air (weight of the product—185 g, mp. 108° C.-110° C.). The filtrate is cooled the second time during 24 hours. The second part of the precipitate was filtered off and dried in air (weight of the product is 55 g. mp. 106° C.-108° C.). The synthesized monomer can be obtained in a solid state as white-grey crystals for easy storage and later use.

Molds for gelcasting are prepared in a separable operation, Step 2. Three conventionally employed materials for such molds are hydrocolloid powder, silicone and wax. Silicone provides a single use whereas hydrocolloid and wax provide multiple uses. Wax has some dimensional instability compared with the other two. Therefore, agar or agarose hydrogel powders are preferred.

The priorities for mold material in the context of gelcasting in the present circumstance are elastic properties, adequate strength and interaction with the ceramic slurry. The elastic properties and strength can be provided by use of the agar or agarose hydrogel powders. In addition, flexibility can be increased by adding saccharides. Borax can be added as a cross-linking and strengthening agent. Microcellulose also can provide a strengthening agent; and glycerine can function as a plasticizer, which can also replace water to some degree.

Regarding interaction with the ceramic slurry, the presence of oxygen either trapped on the mold or diffused through the mold can inhibit polymerization. Exclusion of oxygen, not inherently present in the agar or agarose hydrocolloid, can obviate such inhibition. Extraction of water from the ceramic slurry into the mold can also interfere with the slurry composition. Relatively thick walled hydrocolloid molds reduce moisture loss. Further, fillers in the hydrocolloid reduce sucking of moisture from the slurry into the mold.

The following reagents for the hydrocolloid molds preparation are listed here:
Agar or agarose;
D-fructose;
Distilled water;
Borax;
Carboxymethylcellulose sodium salt;
Guar gum.

In preparation of hydrocolloid molds, a 5% agar aqueous solution (for example 2.5 g of agar+47.5 g of $H_2O$) is mixed and defoamed in a container. The solution is heated to 90° C. in a microwave oven for 90 seconds and mixed after one minute. D-fructose (4× agar quantity—10 g in the described procedure) is then added. Optionally other additives, borax (10 wt % with respect to agar content), carboxymethylcellulose sodium salt (up to 5 wt % with respect to agar), guar gum (up to 5 wt % with respect to agar), and ammonium persulfate (10 wt % with respect to agar) may advantageously be added. The solution can then be poured over a prepared model and let stand until the suspension gelates at about 40° C. The mold can then be separated from the model and used in the gelcasting process. Prepared hydrocolloid molds can be stored for use in ethyl alcohol at room temperature for up to a week.

With the non-toxic monomer 3-O-acryloyl-D-glucose and hydrocolloid molds at the ready, gelcasting of green bodies, Steps 3-10, can commence. A slurry is first prepared, Step 3, and mixed, Step 4. The composition of the zirconia slurry in the preferred embodiment includes:

zirconia ceramic powder;
20.5 wt % (with respect to zirconia) of distilled (or deionized) water (solvent);
0.4 wt % (with respect to zirconia) of diammonium hydrocitrate (dispersant);
4.0 wt % (with respect to zirconia) of 3-O-acryloyl-D-glucose (monomer);
0.5 wt % (with respect to monomer) of N,N,N',N'-tetramethylethylenediamine (activator of polymerization).

These proportions appear to provide the best performance for precisely filling the detailed features of a mold and having the highest solid loading possible. Precise filling is achieved with low viscosity and low yield stress. Increasing the ratio of monomer in the slurry increases both viscosity and yield stress. The additives also impact the rheological performance. High solid loading of the ceramic suspension improves the physical properties of the final appliance. It is also preferred to make slurry batches which are just enough to fill the mold.

The components should be added, Step 3, in the following sequence: water, dispersant, monomer, activator, ceramic powder. In the preferred process, six grinding balls of 1 cm diameter are also added to the mixture. The mixture is then processed, Step 4, in a planetary ball mill for 60 minutes at 300 rpm. After mixing, the slurry is transferred to a suitable container, Step 5, for defoaming and degassing. A planetary centrifugal mixer is conveniently used.

Preferably mixing of the components of the slurry is first accomplished without an initiator for polymerization. Once the slurry is mixed and degassed, ammonium persulfate is mixed into the slurry. 0.3 wt % (with respect to the monomer) of ammonium persulfate (initiator of polymerization) is added to the degassed slurry. It is recommended to use 5% aqueous solution of ammonium persulfate. The amount of added initiator should be carefully controlled as extremes are easily achieved.

As gelation impacts the ability to precisely fill the mold, the initiated slurry should be quickly mixed with the initiator and quickly degassed again all as one process, Step 6. These operations preferably should be performed for periods measured in seconds.

After the second degassing, Step 6, the initiated slurry is poured into prepared hydrocolloid molds, Step 7. This process is to be performed without any delay. As the initiator has been mixed in, polymerization begins in situ, Step 8. During gelation in the mold, the polymerization process can be inhibited by the presence of oxygen. Degassing described above helps to reduce the inhibiting effect of oxygen on polymerization of the casting. On the surfaces, spraying the hydrocolloid mold with initiator solution before charging the mold with slurry promotes polymerization at the interface of the slurry with the mold surface. Using a glass or hydrocolloid cover touching the slurry at the mold opening or spraying the exposed slurry with initiator, both providing a barrier to oxygen on exposed surfaces of the slurry charge in the mold, promotes polymerization at that otherwise exposed surface.

After filling with ceramic slurry, the mold is placed in a dryer (30 min 35° C.+30 min 30° C.). The slurry remains in the mold until the in situ polymerization process ends. With the above proportions of initiator to monomer, removal of the gelled body from the mold may be appropriate after about one hour in the mold. Once gelation is complete, the resulting thick gelled body is removed from the mold, Step 9. The moisture content in the body just after its gelation equals about 14 wt %. This amount of moisture occupies about 51 vol % of the body. With this amount of water, it is to be carefully and uniformly evaporated from the whole volume of the sample.

Drying of ceramic green bodies is a very import stage in gelcasting ceramic technology, reported to frequently defeat practical commercialization of products. In order to uniformly evaporate water from the zirconia green body obtained by gelcasting, a climate chamber may be used. The zirconia green body from the hydrocolloid mold is placed in a climate chamber and dried, Step 10. The initial conditions in the climate chamber are set at a temperature of 30° C. with a relative humidity of 85%. These conditions are sustained for one hour to normalize the state of the green body. The humidity is then continuously decreased to 60% and the temperature increased by incremental amounts to 50° C. over a period of 16 hours. This is a drying rate of about 1.5% per hour. Once reaching 50° C., the climate chamber is maintained at that temperature for seven hours in order to remove all residual moisture.

The resulting dried green body, principally of zirconia held by polymerized material, can be machined to final form with a hand-held rotary grinding and polishing tool, Step 11. The density of the body has been found to be about 48% of the theoretical density, calculated using the zirconia powder component. The inlet of the dried elements can be removed as well as all roughness and anomalies. A light microscope may be employed as would be employed for the finishing of otherwise manufactured crowns and bridges. However, rather than working on a fully hardened ceramic body, machining is performed on a relatively soft, easily machined green body. As little removal of material is likely to be required, the "machining" is principally a hand-held grinder/polisher operation.

Converting the green body to a useful crown or bridge requires burnout of the polymer binder from the body and sintering the zirconia to achieve a fully densified, polycrystalline ceramic element, Step 12. The selection of an appropriate heating program is significant in obtaining nonporous samples. During polymer removal, a rapid heating rate (e.g., 5° C./min) can result in a porous structure because of the accumulation of gases, cracks and delamination in the body. Polymer removal is accomplished by raising the green body temperature from 30° C. to 550° C. to 600° C. inclusive at between 1° C./min. to 2° C./min. inclusive. At about 550° C., all polymer has been turned to $CO_2$ and $H_2O$ with small amounts of $NO_2$, leaving zirconia.

Conveniently, the heating may then continue, Step 12, to perform sintering of the zirconia into a polycrystalline ceramic element in a conventional process. The zirconia body can be heated from 600° C. to 1550° C. at a rate of 5° C./min. The sintering continues at 1550° C. for one hour. The body can then be cooled at a rate of 5° C./min. Final touch-up, Step 13, e.g., deburring, polishing, glazing and coloration may easily be performed as needed on the hard ceramic body to result in a patient ready final product, Step 14.

Thus, a process has been presented for the gelcasting of dental restorations. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:
1. A process for creating dental restorations, comprising creating a mold for the restoration;
preparing a slurry of zirconia powder, a monosaccharide based monomer, water, a dispersant, a polymerization activator and a polymerization initiator;
gelcasting the slurry with polymerization of the monosaccharide based monomer to a green body in the mold of the dental restoration;
spraying the mold with the initiator before gelcasting the slurry;
sintering the green body to form the dental restoration.
2. The process of claim 1, the monosaccharide based monomer being 3-O-acryloyl-D-glucose.
3. The process of claim 1 further comprising
providing a barrier to oxygen on the slurry in the mold.
4. The process of claim 1 further comprising
drying the green body before sintering in a climate chamber including presenting the green body to a humidity of 85% in the climate chamber and reducing the humidity in the climate chamber by 1.5% per hour to a humidity in the climate chamber of 60%.
5. The process of claim 4, drying the green body further including bringing
the temperature by incremental amounts to 50° C. continuously during reduction of the humidity in the climate chamber.
6. The process of claim 5, drying the green body further including retaining the humidity in the climate chamber at 60% and the temperature at 50° C. for seven hours.
7. The process of claim 6, drying the green body further including normalizing the green body at 30° C. in the climate chamber with the climate chamber at 85% humidity before reducing the humidity in the climate chamber.
8. The process of claim 4 further comprising
burning out the polymerized 3 monosaccharide based monomer by heating the dried green body at a rate of between 1° C./min. and 2° C./min. inclusive to between 550° C. and 600° C. inclusive before sintering.
9. A process for creating dental restorations, comprising creating a mold for the dental restoration;
preparing a slurry of zirconia ceramic powder in water including 4.0 wt % (with respect to zirconia) of 3-O-acryloyl-D-glucose, a dispersant, a polymerization activator and a polymerization initiator;
gelcasting the slurry with polymerization of the 3-O-acryloyl-D-glucose to a green body in the mold of the dental restoration with a moisture content of 14 wt % just after gelation;
sintering the green body to form the dental restoration.
10. The process of claim 9, preparing the slurry of zirconia with the water at 20.5 wt % (with respect to zirconia).
11. The process of claim 9, preparing the slurry of zirconia further including the dispersant being 0.4 wt % (with respect to zirconia) of diammonium hydrocitrate, the activator of polymerization being 0.5 wt % (with respect to 3-O-acryloyl-D-glucose) of N,N,N',N'-tetramethylethylenediamine (activator of polymerization) and the polymerization initiator being 0.3 wt % (with respect to 3-O-acryloyl-D-glucose) of ammonium persulfate.
12. The process of claim 9, preparing the slurry of zirconia further including the water at 20.5 wt % (with respect to zirconia), the dispersant being 0.4 wt % (with respect to zirconia) of diammonium hydrocitrate, the activator of polymerization being 0.5 wt % (with respect to 3-O-acryloyl-D-glucose) of N,N,N',N'-tetramethylethylenediamine (activator of polymerization) and the polymerization initiator being 0.3 wt % (with respect to 3-O-acryloyl-D-glucose) of ammonium persulfate.

13. A process for creating dental restorations, comprising creating a hydrocolloid mold for the dental restoration;
preparing a slurry of zirconia powder and 3-O-acryloyl-D-glucose;
gelcasting the slurry with polymerization of the 3-O-acryloyl-D-glucose to a green body in the mold of the dental restoration;
drying the green body;
machining the dried green body to the form of the dental restoration;
burning out the polymerized 3-O-acryloyl-D-glucose by heating the dried green body to between 550° C. and 600° C. inclusive before sintering;
sintering the machined green body at 1550° C. for one hour to form the dental restoration.

14. A process for creating dental restorations, comprising creating a mold for the restoration;
preparing a slurry of zirconia powder, a monosaccharide based monomer, water, a dispersant, a polymerization activator and a polymerization initiator;
gelcasting the slurry with polymerization of the monosaccharide based monomer to a green body in the mold of the dental restoration;
sintering the green body to form the dental restoration; and
drying the green body before sintering in a climate chamber including presenting the green body to a humidity of 85% in the climate chamber and reducing the humidity in the climate chamber by 1.5% per hour to a humidity in the climate chamber of 60%.

15. The process of claim 14 further comprising providing a barrier to oxygen on the slurry in the mold.

16. The process of claim 14, drying the green body further including bringing the temperature by incremental amounts to 50° C. continuously during reduction of the humidity in the climate chamber.

17. The process of claim 16, drying the green body further including retaining the humidity in the climate chamber at 60% and the temperature at 50° C. for seven hours.

18. The process of claim 17, drying the green body further including normalizing the green body at 30° C. in the climate chamber with the climate chamber at 85% humidity before reducing the humidity in the climate chamber.

19. The process of claim 14 further comprising burning out the polymerized monosaccharide based monomer by heating the dried green body at a rate of between 1° C./min. and 2° C./min. inclusive to between 550° C. and 600° C. inclusive before sintering.

20. The process of claim 14, preparing the slurry of zirconia with the water at 20.5 wt % (with respect to zirconia).

* * * * *